United States Patent [19]

Bailly

[11] Patent Number: 4,461,099

[45] Date of Patent: Jul. 24, 1984

[54] MOLDED ODOR-ABSORBING LAMINATE

[76] Inventor: Richard L. Bailly, Beechwood Cir., Boxford, Mass. 01921

[21] Appl. No.: 470,606

[22] Filed: Feb. 28, 1983

[51] Int. Cl.³ .................. A43B 13/38; A43B 7/06; B32B 5/06; B32B 5/18

[52] U.S. Cl. .................. 36/44; 156/148; 156/222; 428/281; 428/282; 428/283; 428/286; 428/287; 428/300; 428/314.4; 428/316.6; 428/317.9

[58] Field of Search .................. 36/44; 428/234, 235, 428/244, 282, 283, 284, 286, 287, 300, 304.4, 314.4, 314.8, 316.6, 317.9, 280, 281; 156/148, 222

[56] References Cited

U.S. PATENT DOCUMENTS

| | | | |
|---|---|---|---|
| 3,842,519 | 10/1974 | Lapidus | 36/44 |
| 3,852,897 | 12/1974 | Bridge et al. | 36/44 |
| 4,062,131 | 12/1977 | Hsiung | 36/44 |
| 4,099,342 | 7/1978 | Singh | 36/44 |
| 4,137,110 | 1/1979 | Singh | 428/244 |
| 4,185,402 | 1/1980 | Digate | 36/44 |
| 4,186,499 | 2/1980 | Massok, Jr. et al. | 36/44 |
| 4,192,086 | 3/1980 | Sichak | 36/44 |
| 4,223,458 | 9/1980 | Kihara | 36/44 |
| 4,235,027 | 11/1980 | Singh | 36/44 |
| 4,250,172 | 2/1981 | Mutzenberg et al. | 428/244 |
| 4,257,176 | 3/1981 | Hartung et al. | 36/44 |

*Primary Examiner*—William J. Van Balen
*Attorney, Agent, or Firm*—Edmund R. Pitcher

[57] ABSTRACT

A laminate is formed by needling a layer of hydrophobic fibers through a middle odor-absorbing layer into a bottom layer of closed-cell foamed thermoplastic. The laminate may be thermoformed to produce articles having a surface shape conforming to the contours of a region of the human body such as resilient supportive innersoles, soft casts or splints, and impact-absorbing pads. Such articles, in addition to their usual function, absorb odors significantly and wick perspiration away from the skin. Innersoles made from the laminates resist delamination and disintegration even when used in athletic footwear.

20 Claims, 6 Drawing Figures

MOLDED ODOR-ABSORBING LAMINATE

BACKGROUND

This invention relates to improved materials for use in close contact with the human body such as innersoles, casts and splints, impact-absorbing pads, and other articles which are exposed to body perspiration and odor-causing substances. More particularly, the invention relates to an odor absorbing laminate having a surface conforming to the contours of a selected region of the body which wicks perspiration from the body.

It has long been a goal to provide various products used on the body with the capacity to minimize the undesirable effects of body perspiration, moisture and odor. Clothing and shoes, for example, often include designed features, fabrics, and materials directed to dispersing uncomfortable moisture from body surfaces. Polypropylene and other synthetic, hydrophobic fabrics are currently used in undergarments designed for wear during athletic activity because such fabrics are good insulators and wick perspiration away from the body.

Another example is the numerous commercially available, odor-absorbing shoe innersoles. Webs of material containing activated charcoal can make effective odor-absorbing innersoles but are usually too fragile to be effective for more than a short time. If such webs are placed in a laminate of sturdier materials, however, the other layers or the adhesives employed often interfere with the efficacy of the odor-absorbing layer. Generally, fabrication of such odor-absorbing laminates has been limited to the production of flat sheets from which innersoles or other shapes are cut. Because of the requirements of vapor and liquid permeability, the necessity of a large surface area of activated carbon being available for absorption, and the general fragility and design requirements of odor-absorbing materials, products used on the body such as casts, splints, pads, and the like which have odor absorbing properties have not been available commercially.

Greatest effort in this area apparently has been concentrated in innersole technology as is disclosed, for example, in U.S. Pat. Nos. 3,852,897, 4,062,131, 4,099,342, 4,137,110, 4,185,402, and 4,192,086. However, none of these deal with the peculiar problems of molding laminates that have a close-cell foamed plastic layer, and, generally, the innersoles shown can be improved greatly in their capacities for dispersing perspiration and absorbing odor.

Accordingly, it is an object of this invention to provide a laminate that is sturdy, has enhanced odor-absorbing qualities, and is comfortable when maintained in direct contact with the human body. Another object is to provide a material which may be molded to form products for use on the body, such as shoe insoles, casts, impact absorbing pads, and similar products.

SUMMARY OF THE INVENTION

The invention in its broadest aspects comprises a trilayered laminate designed for molding to form products used in contact with the human body. The laminate is used to fabricate, for example, innersoles, devices for immobilizing portions of the body during healing or therapy such as casts or splints, pads for impact-absorption such as are used on the interior of athletic wear for contact sports, low density thermally-insulating innerwear suitable for use in cold climates, and other articles. Products made in accordance with the process disclosed herein may be designed to exploit properties characteristic of foam plastic materials such as impact-absorption, water-repellance, thermal-insulating properties, and resilient or cushioned support. In addition, products of the invention very significantly absorb odors and odor-carrying chemicals. They are exceptionally comfortable when maintained in contact with the body for extended periods because of a soft inner layer which wicks perspiration away from the skin and aids in the mechanism of odor absorption. Also, products of the invention resist delamination and disintegration even when used as an odor-absorbing supportive cushioned innersole in an athletic shoe.

These features are achieved by providing a laminate having at least one surface conforming substantially to the contours of a surface region of the human body, e.g., the sole of the foot, a shoulder, etc. The laminate comprises a foamed thermoplastic first layer, preferably closed-cell, with a thermoformed inner surface comforming to the contours of a region of the body, a second, middle layer affixed to the thermoformed surface comprising activated charcoal particles disposed within a binder, and a third innermost layer. The third layer comprises hydrophobic fibers of polypropylene, polyester, or the like, needle punched into and preferably through the second layer, which form a substantially continuous non-woven soft layer defining a multiplicity of air pockets and paths for wicking perspiration away from the skin and for exposing the surface of activated carbon in the second layer to odor-causing substances.

In a preferred embodiment, the laminate takes the form of an odor-absorbing innersole for footwear molded to fit within, for example, an athletic shoe or boot. The innersole has an upper thermoformed surface conforming to the surface shape of the human sole including an arch support and heel cup. In another embodiment the laminate takes the form of a "soft cast", splint, or pad.

The odor-absorbing layer preferably comprises cellulosic fibers and activated carbon particles disposed within a binder of latex or the like. The carbon content is preferably at least about 20% by weight but can be up to about 60% by weight. A fourth layer of hydrophilic fiber may be needle-punched into the exposed outermost surface of the first foam plastic layer.

The products of the invention may be manufactured by placing surfaces of the first and second layers in contact, optionally with an adhesive, placing a layer of fibers atop the second layer, and needle-punching the fibers to form the third layer, to reinforce the odor-absorbing layer, and to open it up to moisture and odor-causing chemicals. Preferably, and particularly in the construction of the innersole embodiment, the fibers also tie the first and second layers together and thus penetrate the odor-absorbing layer and the foamed layer. This laminate is then thermoformed by applying heat to the foamed layer to soften it and then imposing a surface contour to at least one surface, e.g., in a cooled mold. By selecting a suitable foamed plastic material such as the closed cell, cross-linked ethylene vinyl acetate or polyethylene foam, it is possible to shape the heated laminate directly about a body part such as an arm, leg, or ankle to form a soft cast.

BRIEF DESCRIPTION OF THE DRAWINGS

Other objects, features and advantages of the invention will be apparent from the following description and from the drawing wherein like reference characters in the respective drawn figures indicate corresponding parts. In the drawing.

DESCRIPTION OF THE PREFERRED EMBODIMENTS

Figure 1:
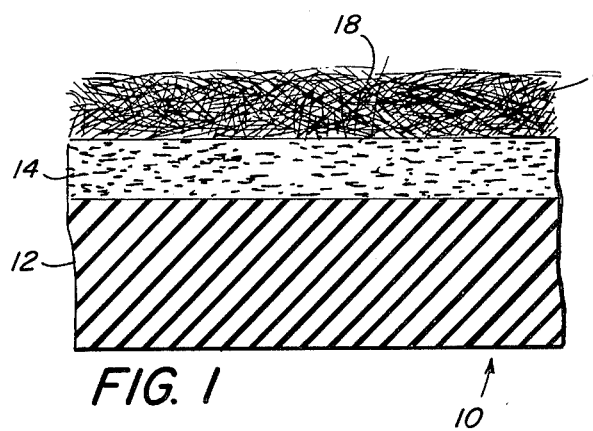
FIG. 1 is a schematic cross-section of a first stage in the preparation of the laminate of the invention, showing three layers of material.
Figure 2:
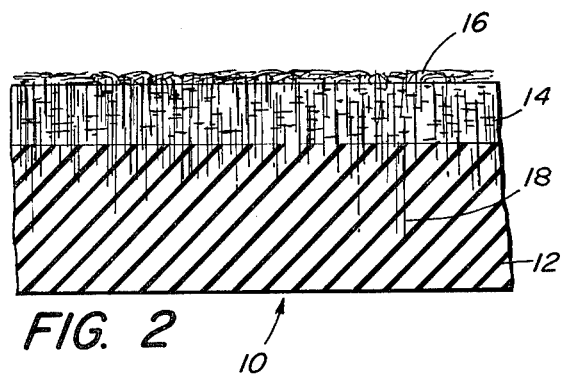
FIG. 2 is a schematic cross-section of the laminate of FIG. 1, after the layers are needled together.
Figure 3:
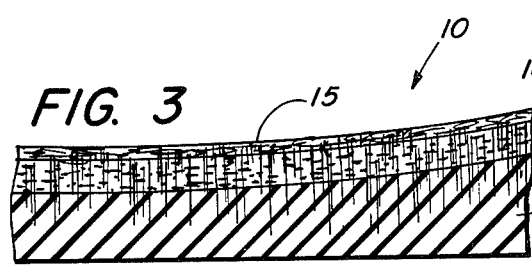
FIG. 3 is a schematic cross-section of the laminate of FIG. 2 after thermoforming.

As shown in FIGS. 1-3, the laminate 10 illustrating the invention has at least three layers. The first or bottom layer 12, which is farthest from the skin in use, comprises a sheet of a closed-cell foamed thermoplastic. The middle, or second, layer 14 is a sheet of odor-absorbing material such as is described in U.S. Pat. No. 3,852,897 comprising a mixture of activated carbon particles and cellulosic fibers in a binder matrix. The third, or top layer 16 is a non-woven mat of hydrophobic fibers 18 such as polyester or polypropylene fibers.

Layer 12 may comprise any one of a number of known thermoplastic foam materials or blends thereof such as polyethylene, ethylene vinyl acetate copolymers, crosslinked polyethylene, acrylics, polyvinyl chloride, polystyrene, and the like. Such foamed, preformed thermoplastic sheet materials are available commercially. The moldable foam plastic layer 12 is selected to achieve the combination of properties best suited for the particular end use of the product. For example, relatively rigid foams such as cross-linked polyethylene closed-cell foam blown with nitrogen and sold under the trademark Plastozote are suitable for making body-fitting soft casts. More flexible foams which provide cushioned support such as Evazote, a cross-linked copolymer of ethylene vinyl acetate and polyethylene blown with pure nitrogen, is well suited for fabricating innersoles. Various foams suitable for these and other purposes are also available from General Foam Corporation.

All of the foam plastic materials useful in the invention are thermoformable. Thus, after heating in an oven or by other means they are softened and can be permanently deformed but in the absence of applied force retain their shape and foam structure. Such materials may be molded or thermoformed in a mold cavity. Alternatively, in the case of certain materials such as the high quality nitrogen blown polyethylene and ethylene vinyl acetate materials sold under the trademarks Plastozote and Evazote, thermoforming can be conducted either in a mold cavity or directly on an exposed surface of the body.

Layer 14 comprises an odor-absorbing, activated carbon-filled matrix which also includes a binder and preferably a filler such as cellulosic fibers. The odor-absorbing matrix must be flexible enough to conform to the molded foam surface to which it is affixed and sufficiently heat resistant to withstand thermoforming temperatures. Many prior art materials will tear when streched about a curved surface during molding and thus cannot be used to mold many products on a commercial scale without a high level of rejects. However, as disclosed below, needling in accordance with the invention significantly adds to the tear strength of fragile materials.

A preferred odor-absorbing layer for use in the invention is available commercially from Purification Products Ltd., a subsidiary of P. Garnett & Sons Ltd., West Yorkshire, England, and is sold under the tradenames "Odasorb" or "Garfil." This material is sold in sheet form and comprises activated carbon fibers and wood pulp fibers in a latex binder. Details of the materials and construction of such odor-absorbing sheets are disclosed in U.S. Pat. Nos. 4,317,110, 4,099,342, and 3,852,897, the disclosures of which are incorporated herein by reference. Unlike the odor-absorbing layers of these patents, the layer 14 used herein need not include an adhered fabric web. The content of activated carbon in the layer 14 is preferably at least 20%, and the more carbon the better provided that the layer's tear strength does not deteriorate to the point where the web is damaged during thermoforming.

The third layer 16 comprises a multiplicity of hydrophobic fibers such as polypropylene or polyester. Other hydrophobic fibers may be used. The length of the fibers depends upon the overall thickness of the article being manufactured. For innersoles which after molding have a thickness ranging from about one-eighth inch to about five-eighths inch, fibers on the order of one-half inch long suffice. Longer fibers may be used on thicker products such as impact-absorbing pads. The fibers are preferably thin, e.g., 10 microns in diameter or less, and are used at a density on the order of 2-10 ounces per square yard of laminate, preferably about 6 ounces per square yard. Such hydrophobic fibers are known to have the ability to wick perspiration away from the body along the axis of the fiber.

As is shown in FIG. 1, in the manufacturing process of the invention the thermoformable foam layer 12 and odor-absorbing layer 14 are placed in contact, optionally with an interposed film of thermoplastic or other adhesive to aid in lamination, and the fibers 18 are scattered randomly about the upper surface of layer 14 to form an intermingled fiber mat. The layer 16 is formed and joined to layer 14 during the needling process wherein the fibers are threaded into at least odor-absorbing layer 14 and preferably into foam layer 12. As shown in FIG. 2, the fibers 18 are locked together to form a soft but sturdy top layer 16 comprising a substantially continuous non-woven layer defining a multiplicity of air pockets. The fibers needled downwards through the layers 14 and 12 strongly bond all three layers together. The needling procedure, by punching holes and imbedding water-transporting fibers downward through the odor-absorbing layer 14, makes the odor-absorbing layer 14 and the activated carbon particles it contains readily accessible to moisture and odor-causing substances from the skin. Thus, there is no need to form openings for the purpose of exposing the activated carbon such as is disclosed in much of the prior art. The needled fibers also significantly reinforce the cellulosic web 14, thereby making it more resistant to tearing and delamination. The use of the fibers permits one to mold the laminate to define fairly sharp corners without tearing the odor-absorbing layer 14.

Figure 4:
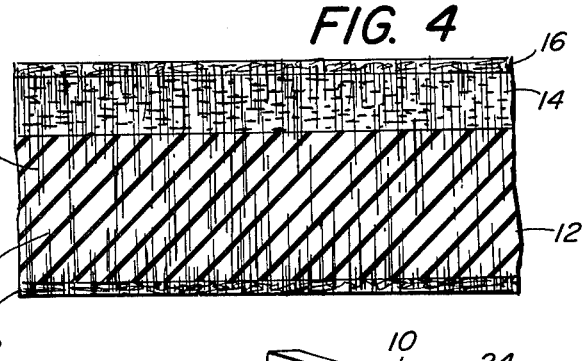
FIG. 4 is a schematic cross-section similar to FIG. 2 of a second embodiment of the invention having four layers.

The laminate 10 shown in FIG. 2 may then be thermoformed into a desired shape conforming to a surface region of the body. Thermoforming is conducted by heating the needled laminate to a temperature sufficient to soften layer 12 without softening fibers 18 and without melting the plastic matrix of the foam or destroying the foam structure. The precise temperature employed depends upon the particular type of foam plastic material involved. As illustrated in FIG. 4, thermoforming may be done in a cooled mold 22 by bringing the upper half 24 and the lower half 26 together on the preheated blanks 10. This action converts the cross-section shown in FIG. 2 to the cross-section shown in FIG. 3. As indicated generally in FIG. 3, heating the laminate 10 reduces the thickness of layer 12 and also relieves internal stress. The compression exerted by the mold will lock any fibers 18 penetrating the foam layer 12 in place by compressing the plastic foam. Upwardly facing surface 15 of layer 14 conforms to the mold shape. Layers 14 and 16 in turn conform substantially to the shape of surface 15.

FIG. 4 shows a variation of the laminate of FIGS. 1–3. In this embodiment, a fourth layer 28 is added to the laminate 10. The layer 28 is located adjacent the bottom foamed plastic layer 12, that is, opposite the odor-absorbing layer 14. This fourth layer 28 during manufacture originally takes the form of a mat of unwoven hydrophilic fibers 30, e.g., of rayon or cotton, which are needled into the bottom surface of foam plastic layer 12 and may at least in part overlap the vertical extent of hydrophilic fibers 18. The laminate of FIG. 4 may be thermoformed in the same way as that of FIGS. 1–3. The hydrophilic fourth layer 28 assists the moisture dispersion of the laminate that is initiated by the hydrophobic first layer 16. Thus, moisture's travel from the body is initiated by the hydrophobic fiber first layer 16. The passage of the moisture through the odor-absorbing layer 14 and into the foam layer 12 is facilitated by the openings created by the needling process. Finally, the hydrophilic layer 28 enhances the passage of moisture by absorption and subsequent evaporation.

Figure 5:
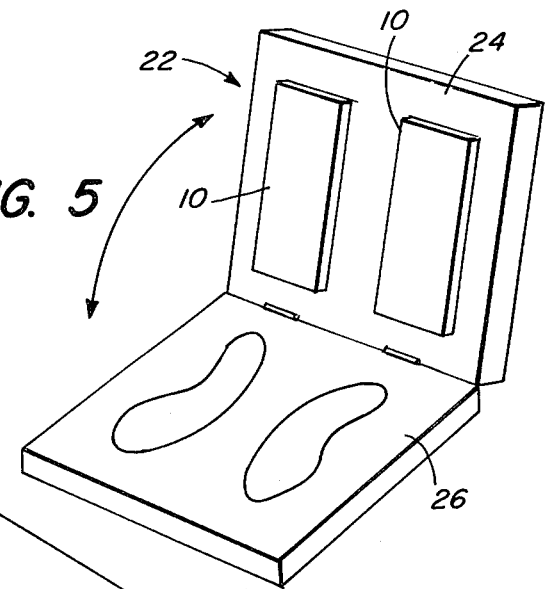
FIG. 5 shows blanks of the laminate of FIG. 2 in a mold prior to molding innersoles.

The laminates of either FIG. 2 or FIG. 4 may be molded in ways other than that illustrated in FIG. 5. One example is that certain foamed thermoplastics such as the cross-linked, nitrogen-blown polyethylene sold under the trademark Plastozote may after heating be pressed directly onto and shaped about an exposed part of the body such as a knee, ankle, or forearm without burning the skin or inducing severe discomfort. Laminates made with such materials in accordance with the invention make excellent, substantially odor-free soft casts and splints.

Thus the invention provides a laminate with superior odor-absorbing capability that is comfortable in prolonged contact with the skin. Its needle-punched structure enhances its odor-absorbing effectiveness and the dispersion of perspiration. It also improves the bonding of the layers of the laminate so that delamination does not occur during molding or during use and reinforces the odor-absorbing layer. The needling and subsequent heating also relieve stress and cause the foam layer 12 to shrink slightly thereby locking the fiber in place. The laminate accordingly can withstand rough use. Furthermore, unlike odor-absorbing structures of the prior art, the laminate of the invention may be shaped readily to conform to a surface region of the body on which it will be used. By selection of the foam, it is possible to provide a rigid cushioned support for a body part, to provide impact absorption capability, or to provide thermal insulation capability as desired. Casts and pads made in accordance with the invention help eliminate perspiration and odor problems traditionally encountered with such products.

Figure 6:
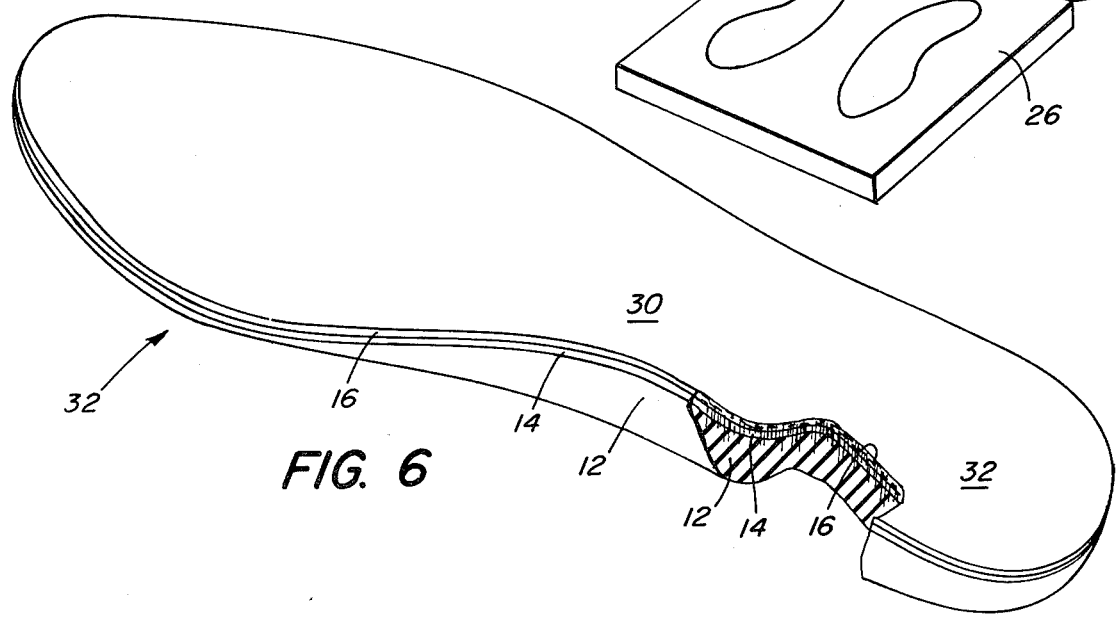
FIG. 6 illustrates an innersole, partly in cross-section, embodying the invention.

A molded resiliently supportive, odor-absorbing innersole for use in footwear generally, but particularly in athletic footwear, is shown in FIG. 6 of the drawing. This product 32 includes an arch support section 30 and a heel cup section 32. Layers 12, 14, and 16, shown in cross-section, are constructed in accordance with the foregoing disclosure.

The molded innersole thus produced is strong and durable enough to be incorporated directly into the sole of a shoe during its manufacture. Furthermore, innersoles of this type have been tested to assess their odor-absorbing capability verses unmolded, commercially available odor-absorbing products. The results of these tests indicate that innersoles made in accordance with the invention are significantly improved with respect to both the amount of odor-causing vapor adsorbed and in the retention of the vapor.

The invention may be embodied in other specific forms without departing from the spirit and scope thereof. Accordingly, other embodiments are within the following claims.

What is claimed is:

1. A laminate having a surface conforming substantially to the contours of a surface region of the human body, the laminate comprising:
   a foamed thermoplastic first layer having a thermoformed surface conforming to the contours of said body surface region;
   a second layer affixed to and conforming to the contours of said thermoformed surface comprising a multiplicity of activated charcoal particles disposed within a binder; and
   a third layer comprising a multiplicity of hydrophobic fibers, a substantial fraction of which penetrate said second layer, said fibers together comprising a non-woven, substantially continuous layer affixed to said second layer and defining a multiplicity of air pockets;
   said layers being effective to cooperate in use to maintain fibers of said third layer in contact with perspiration from said body surface, to wick perspiration and odor-causing substances away from said body surface, and to absorb a substantial fraction of said odor-causing substances.

2. The laminate of claim 1 comprising an innersole wherein said thermoformed surface conforms substantially to a portion of the sole of the human foot and includes an arch support section.

3. The laminate of claim 2 wherein said innersole further includes a heel cup section.

4. The laminate of claim 1 comprising means for immobilizing a region of the human body.

5. The laminate of claim 1 comprising an impact-absorbing pad.

6. The laminate of claim 1 wherein said foamed thermoplastic is selected from the group consisting of polyethylene, ethylene-vinyl acetate copolymers, cross-linked polyethylene, and mixtures thereof.

7. The laminate of claim 1 wherein said fibers comprise a polymer selected from the group consisting of polypropylenes and polyesters.

8. The laminate of claim 1 wherein said second layer comprises cellulosic fibers and at least about 20% by weight active carbon disposed within a latex binder.

9. The laminate of claim 1 further comprising a multiplicity of hydrophilic fibers which penetrate said first layer and together comprise a fourth layer disposed on the surface of said first layer opposite said thermoformed surface.

10. The laminate of claim 1 wherein said foamed thermoplastic comprises a closed-cell foam.

11. The laminate of claim 9 wherein a fraction of said hydrophobic fibers penetrate said first layer and overlap with said hydrophilic fibers.

12. A method of forming an article of manufacture having a surface conforming substantially to the contours of a surface region of the human body for wicking perspiration away from said surface region and absorbing odor-causing substances, said method comprising the steps of:
   A. placing a surface of a foamed thermoformable sheet in contact with a surface of a sheet of odor-absorbing material comprising activated charcoal particles disposed within a binder;
   B. forming a laminate by needle-punching hydrophobic fibers through said odor-absorbing material and into said thermoplastic sheet to produce a nonwoven, substantially continuous, fiber layer affixed to the surface of said odor-absorbing sheet material opposite said thermoformable sheet, and to increase the resistance to delamination of said sheets and said odor-absorbing material;
   C. heating the product of step B to soften said thermoformable sheet; and
   D. imposing a surface contour to at least the side of said laminate comprising said fiber layer, said surface contour substantially conforming to said body surface region.

13. The method of claim 12 wherein step D is effected by compression molding.

14. The method of claim 12 wherein said thermoformable sheet comprises a polymer selected from the group consisting of polyethylene, ethylene-vinyl acetate copolymers, cross-linked polyethylene, and mixtures thereof.

15. The method of claim 12 wherein said fibers comprise a polymer selected from the group consisting of polypropylenes and polyesters.

16. The method of claim 12 wherein said sheet of odor-absorbing material comprises at least about 20% by weight activated carbon and cellulosic fibers in a latex binder.

17. A laminate for use in the production of thermoformed articles for placement in close proximity to the body, said laminate comprising:
   a thermoformable, closed-cell, foamed thermoplastic first layer;
   an odor-absorbing second layer comprising activated carbon particles in a binder affixed to a surface of said first layer; and
   a third layer comprising a multiplicity of hydrophobic fibers, a substantial fraction of which penetrate said second layer and said first layer, said fibers together comprising a soft, non-woven, substantially continuous layer affixed to said second layer and defining a multiplicity of air pockets.

18. The laminate of claim 17 wherein said first layer comprises a polymer selected from the group consisting of polyethylene, ethylene-vinyl acetate copolymers, cross-linked polyethylene, and mixtures thereof.

19. The laminate of claim 17 wherein said second layer comprises at least about 20% by weight activated carbon and cellulosic fibers in a latex binder.

20. The laminate of claim 17 wherein said fibers comprise a polymer selected from the group consisting of polypropylenes and polyesters.

* * * * *